US00PP21211P2

(12) United States Plant Patent
Jensen

(10) Patent No.: US PP21,211 P2
(45) Date of Patent: Aug. 17, 2010

(54) ***ASTER* PLANT NAMED 'DASDEBI'**

(50) Latin Name: ***Aster novi-belgi* (now *Symphyotrichum novi-belgii*)**
Varietal Denomination: Dasdebi

(75) Inventor: Bent Juhl Jensen, Malling (DK)

(73) Assignee: Gartneriet Raahoj, Malling (DK)

( * ) Notice: Subject to any disclaimer, the term of this patent is extended or adjusted under 35 U.S.C. 154(b) by 0 days.

(21) Appl. No.: 12/380,347

(22) Filed: Feb. 26, 2009

(51) Int. Cl.
*A01H 5/00* (2006.01)

(52) U.S. Cl. ..... Plt./355

(58) Field of Classification Search ..... Plt./355
See application file for complete search history.

*Primary Examiner*—Susan B McCormick Ewoldt
(74) *Attorney, Agent, or Firm*—Foley & Lardner LLP

(57) ABSTRACT

A new distinct cultivar of *Aster* plant named 'DASDEBI', characterized by its upright and inverted conical plant habit; yellow-green and gray-green foliage; decorative, composite-type inflorescence with about 250 to 300 violet-blue-colored ray florets; and only about 10 to 20 disc florets per inflorescence which are white in color with yellow-orange tips (almost 100% filled capitulae).

2 Drawing Sheets

Latin name of the genus and species of the claimed plant: *Aster novi-belgi* (now *Symphyotrichum novi-belgii*).

Variety denomination: 'DASDEBI'.

BACKGROUND OF THE INVENTION

The present invention relates to a new and distinct cultivar of *Aster* plant, botanically known as *Aster novi-belgii* (now *Symphyotrichum novi-belgii*) of the Asteraceae family, commonly known as Michaelmas Daisy and New York Aster, and hereinafter referred to by the cultivar name 'DASDEBI'.

The new *Aster* cultivar is a product of a planned breeding program conducted by the inventor, Bent Juhl JENSEN, in Malling, Denmark. The objective of the breeding program is to develop a new *Aster* variety with uniform plant growth habit, unique floret colors, and good postproduction longevity.

The new *Aster* cultivar originated from a cross made in a controlled breeding program by the inventor in September of 2006, in Malling, Denmark. The female or seed parent is *Aster novi-belgii* 'VICTORIA MATHILDE' (unpatented, disclosed in pending CPVO Application No. 2006/1898). The male or pollen parent is the unpatented *Aster novi-belgii* seedling selection designated RH 05-108-05. The new *Aster* 'DASDEBI ' was discovered and selected by the inventor as a single flowering plant within the progeny of the stated cross in September of 2007 in a controlled environment in Malling, Denmark. The selection of the new *Aster* 'DASDEBI' was based on its uniform plant growth habit and desirable inflorescence form and ray floret color.

Asexual reproduction of the new *Aster* cultivar by vegetative tip cuttings was first performed in June of 2007 in Malling, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DASDEBI', which in combination distinguish this *Aster* as a new and distinct cultivar:

1. Upright and inverted conical plant habit;
2. Yellow-green and gray-green foliage;
3. Decorative, composite-type inflorescence with about 250 to 300 violet-blue-colored ray florets; and
4. Only about 10 to 20 disc florets per inflorescence which are white in color with yellow-orange tips (almost 100% filled capitulae).

Plants of the new *Aster* 'DASDEBI' differ from plants of female parent, *Aster novi-belgii* 'VICTORIA MATHILDE' (unpatented, disclosed in pending CPVO Application No. 2006/1898) in the characteristics described below:

1. Plants of 'DASDEBI' are more compact than plants of 'VICTORIA MATHILDE';
2. Plants of 'DASDEBI' produce more ray florets than plants of 'VICTORIA MATHILDE'; and
3. Plants of 'DASDEBI' produce violet-blue ray florets whereas plants of 'VICTORIA MATHILDE' produce violet-colored ray florets (RHS N66A).

Plants of the male or pollen parent, the unpatented *Aster novi-belgii* seedling selection designated RH 05-108-05, are unavailable to provide a botanical comparison to plants of the new *Aster* 'DASDEBI'.

Of the many commercial cultivars known to the present inventor, the most similar in comparison to the new *Aster* 'DASDEBI' are 1) *Aster novi-belgii* 'VICTORIA FANNY' (patented, U.S. Plant Pat. No. 13,360 and CPVO Grant No. 11804) and 2) *Aster novi-belgii* 'MILKA' (patented, U.S. Plant Pat. No. 10,602). Plants of the new *Aster* 'DASDEBI' differ from plants of 1) *Aster novi-belgii* 'VICTORIA FANNY' and 2) *Aster novi-belgii* 'MILKA' in the characteristics described in Table 1.

TABLE 1

| Characteristic | New Cultivar 'DASDEBI' | Comparison Cultivar 'VICTORIA FANNY' (patented) | Comparison Cultivar 'MILKA' (patented) |
|---|---|---|---|
| Leaf Shape: | Gladiate | Lanceolate | Elliptic |
| Mature Leaf Color (upper surface): | Yellow-green, RHS 147A | Yellow-green, RHS 147A | Green, RHS 137A to RHS 137B |
| Capitulum Size: | Diameter: 40-60 mm | Diameter: 32.5 mm | Diameter: 24-27 mm |
| Ray Florets | About 250-300 ray florets per inflorescence, which are flat, obelliptic in shape, with rounded, slightly retuse apex | About 190 ray florets per flower, which are narrowly obovate in shape, with rounded apex | About 128-164 ray florets per flower, which are narrowly elliptic in shape, with acute apex |
| Mature Ray Floret Color (upper surface): | Violet-blue, RHS 90B | Violet, RHS 88C | Violet, RHS 85A |
| Disc Florets: | About 10-20 disc florets per inflorescence | About 25-35 disc florets per inflorescence | No disc florets produced. |
| Mature Disc Floret Color: | White, RHS 155A, transitioning to yellow-orange, RHS 17B, at tips | Yellow-green, RHS 151B | N/A |

BRIEF DESCRIPTION OF THE PHOTOGRAPHS

The accompanying photographs illustrate the overall appearance of the new *Aster* 'DASDEBI' showing the colors as true as is reasonably possible with colored reproductions of this type. Colors in the photographs may differ slightly from the color value cited in the detailed botanical description which accurately describe the color of 'DASDEBI'.

DETAILED BOTANICAL DESCRIPTION

Figure 1:
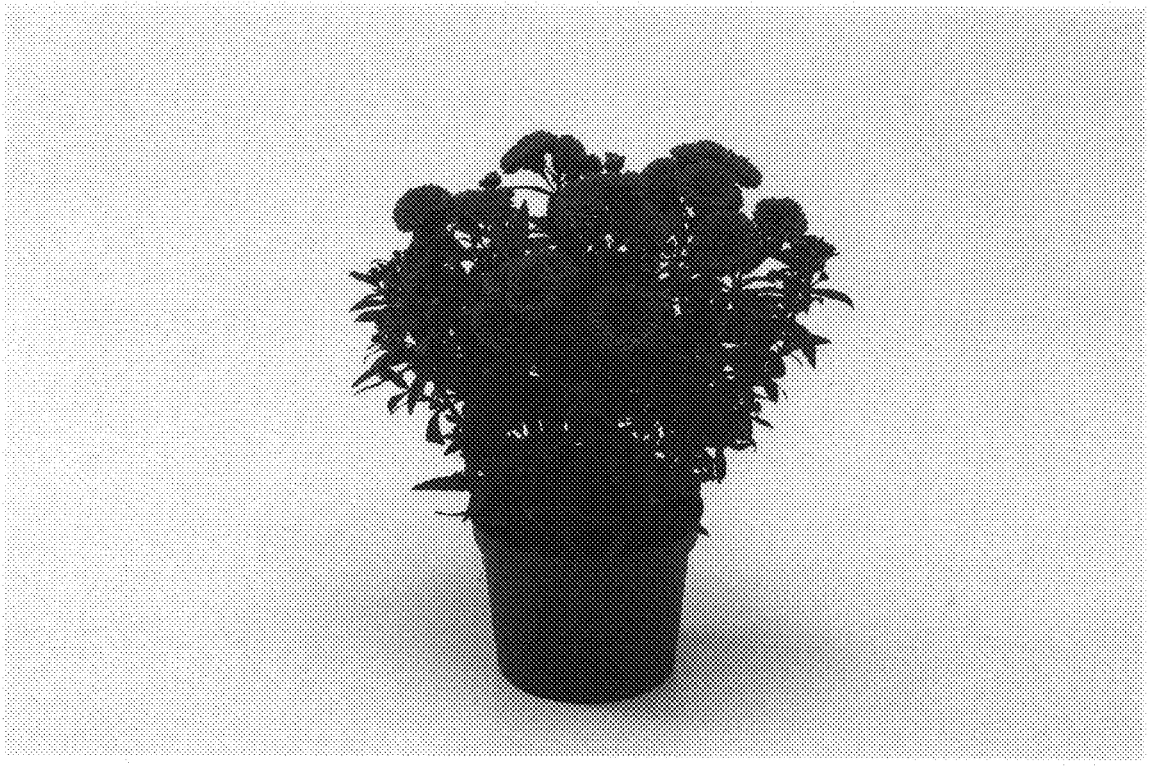
FIG. 1 shows a side view perspective a typical flowering plant of 'DASDEBI' in a 9.5 cm pot, at 14 weeks of age after planting.
Figure 2:
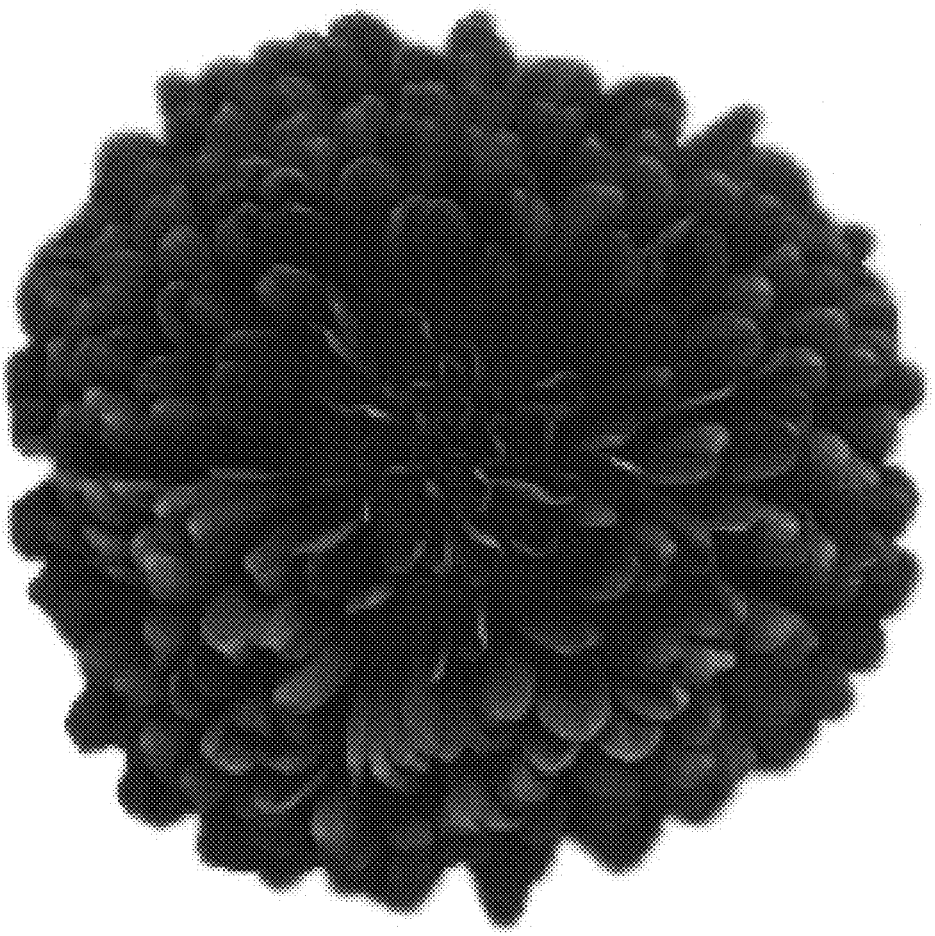
FIG. 2 shows a close-up view perspective of a typical mature inflorescence of 'DASDEBI', at 14 weeks of age after planting.

The new *Aster* 'DASDEBI' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Aster* 'DASDEBI' as grown in a glass-covered greenhouse in Malling, Denmark, under conditions which closely approximate those generally used in commercial practice. 'DASDEBI' plants were grown in 9.5 cm pots in a heated and lighted glass-covered greenhouse with the day temperatures ranging from 18° C. to 20° C. and the night temperature averaging 18° C. 'DASDEBI' plants are grown under short day (9 hour) photoperiodic treatments for five weeks after rooting, followed by long day (20 hour) photoperiodic treatments for five weeks. During the long day (20 hour) photoperiodic treatments, if ambient light level falls below +50 $Wm^2$, a supplementary light at +200 $Wm^2$ is applied. 'DASDEBI' plants 'DASDEBI' plants were pinched twice, and treated twice with the growth retardant Daminozide.

Color references are made to The Royal Horticultural Society Colour Chart (R.H.S.), 4th Edition, except where general colors of ordinary significance are used. Color values were taken under daylight conditions in Malling, Denmark. The age of the 'DASDEBI' plants shown in the photographs and described herein is about 14 weeks.

Classification:

*Botanical.*—*Aster novi-belgii* (now *Symphyotrichum novi-belgii*).

Parentage:

*Female or seed parent.*—*Aster novi-belgii* 'VICTORIA MATHILDE' (unpatented, disclosed in pending CPVO Application No. 2006/1898).

*Male or pollen parent.*—*Aster novi-belgii* seedling selection designated RH 05-108-05 (unpatented).

Propagation:

*Type.*—Vegetative tip cuttings.

*Time and temperature to initiate roots.*—Summer: About 12 days at 21° C. Winter: About 13 days at 21° C.

*Rooting habit.*—Fine, fibrous and freely branching.

*Root color.*—Gray-white, close to RHS 156D.

Plant description:

*General appearance and form.*—Herbaceous, decorative-type potted or bedding plant with upright plant habit. *Aster* inflorescences in composite heads.

*Growth and branching habit.*—Stems upright; inverted conical plant habit. Appropriate for 9 cm to 15 cm containers.

*Growth rate/vigor.*—Vigourous.

*Plant height* (*soil level to top of plant plane*).—About 22 cm.

*Plant width* (*spread*).—About 27 cm.

*Crop time to produce a mature flowering plant.*—After rooting, about 14 weeks are required to produce finished flowering plants in 9.5 cm pots.

Branches:

*Number of branches per plant.*—About 27, with 3 cuttings per pot.

*Quantity of buds and inflorescence per lateral stem.*—1, buds continue to develop when dead flowers are removed.

*Branching habit.*—Freely after pinching.

*Length.*—About 12 cm (including flowers).

*Diameter.*—About 1 mm to 2 mm.

*Internode length.*—About 9 mm. Range about 5 mm to 14 mm.

*Strength.*—Strong.

*Aspect.*—Upright.

*Texture.*—Fimbriate with 3–4 longitudinal furrows.

*Color.*—Yellow-green, RHS 147C.

Foliage description:

*Quantity per branch.*—About 10 to 14.

*Arrangement.*—Single, alternate , sessile.

*Length.*—Up to 4.5 cm.

*Width.*—Up to 10 mm.

*Overall shape of leaf.*—Gladiate.

*Shape at apex.*—Acute.

*Shape at base.*—Decurrent, auriculate ½ clasping.

*Margin.*—Entire.

*Texture.*—Glabrous, smooth, leathery.

*Pubescence.*—Minute scattered hairs along abaxial midvein.

*Color of developing foliage.*—Upper surface: Yellow-green, RHS 145A. Under surface: Yellow-green, RHS 144A.

*Color of mature foliage.*—Upper surface: Yellow-green, RHS 147A. Under surface: Gray-green, RHS 189A.

*Venation pattern.*—None, but prominent central abaxial vein.

*Venation color.*—Upper surface: Green, RHS 145B. Under surface: Gray-green, RHS 189A.

Inflorescence description:

*Appearance.*—Terminal (and few axillary) composite inflorescences held above and beyond the foliage, with about 250 to 300 flat, obelliptic ray florets and only about 10 to 20 tubular disc florets; ray and disc florets arranged acropetally on a capitulum. Inflorescences face upright and form is capitulate in corymbose stands.

*Natural flowering season.*—Under natural season conditions, plants flower in late summer through autumn in Denmark. Season can be extended by vernalization and long day treatments.

*Time to flower.*—About 5 to 6 weeks (longevity of individual inflorescences is dependent on temperature and light conditions).

*Postproduction logevity.*—Inflorescences maintain good color and substance for about 27 days on the plant when in an indoor environment, and may keep longer if temperatures are maintained below 20° C. Inflorescences persistent.

*Quantity of inflorescences.*—About 27 to 37 buds and open inflorescences per plant.

*Fragrance.*—Faint.

*Bud.*—Rate of opening: About 10 per week, for 3 weeks after induction. Length: Up to 5 mm. Diameter: Up to 7 mm. Shape: Globular. Texture: Glabrous. Color: Yellow-green, RHS 147B.

*Peduncle.*—Length: Up to 1 cm. Diameter: 2 mm. Appearance and angle: About 70° from vertical. Strength: Strong. Texture: Glabrous. Color: Yellow-green, RHS 147C.

*Inflorescence.*—Inflorescence (corymb) (height): About 6 to 8 cm. Inflorescence (corymb) diameter About 4 to 6 cm. Capitulum height: About 1.5 cm. Capitulum diameter: About 2.8 cm.

*Quantity of flowers (capitulae) per inflorescence (corymb).*—1 capitulae.

*Ray florets.*—Arrangement and quanity: Imbricate, about 250 to 300 ray florets per capitulum in 9 to 12 whorls of ray florets (depending on light and temperature conditions). Orientation: Initially upright, later mostly horizontal. Aspect: Straight to slightly involute. Appearance: Obelliptic Length: About 11 mm. Width: About 3.5 mm. Overall shape: Flat, obelliptic. Shape at apex: Rounded, slighlty retuse. Shape at base: Attenuate, fused. Margin: Entire. Texture: Upper and under surfaces: Smooth, glabrous, silky. Pubescence: Subtended by numerous short, about 2 mm, white hairs. Color (when opening): Upper surface: violet-blue, RHS 90C. Under surface: violet-blue, RHS 91B. Color (when fully opened): Upper surface: violet-blue, RHS 90B. Under surface: violet-blue, RHS 91D. Fading: Yes, violet-blue, RHS 92D.

*Disc florets.*—Arrangement: About 10 to 20 disc florets, massed at center of capitulum. Length: About 5 mm. Width: About 2 mm. Disc area diameter: About 5 mm. Overall shape: Tubular, with 5 triangular tips. Shape at apex: Acute. Shape at base: Fused to tube. Margin: Entire. Texture: Upper and under surfaces: Scale-like, parchment thin. Pubescence: Subtended by numerous short, about 2 mm, white hairs. Color (when opening): Upper and under surfaces: White, RHS 155A, transitioning to yellow-orange, RHS 17B, at tips. Color (when fully opened): Upper and under surfaces: White, RHS 155A, transitioning to yellow-orange, RHS 17B, at tips.

*Phyllaries.*—Quantity per inflorescence: Involucre, about 40 to 50. Length: About 3 to 6 mm. Width: About 1 to 2 mm. Overall shape: Lanceolate. Apex shape: Acute. Base shape: Truncate Fused. Margin: Entire. Texture: Hairy, setulose edges, verrucose abaxial surface. Color (immature): Upper surface: Green, RHS 137B. Under surface: Green, RHS 137D. Color (immature): Upper surface: Green, RHS 137A. Under surface: Green, RHS 137B.

Reproductive organs:

*Androecium (on disc florets only).*—Stamen number: 5 per floret; fused around style. Stamen length: About 0.5 mm. Anther shape: Narrowly cylindrical, somewhat fused. Anther length: About 0.1 mm. Anther color: Yellow, RHS 8B. Pollen amount: Scarce. Pollen color: Yellow, RHS 8B.

*Gynoecium (on disc and ray florets).*—Pistil number: 1 per floret. Pistil length: About 2 mm. Stigma shape: Cleft. Stigma length: About 0.5 mm. Stigma color: White, RHS N155C. Style length: About 1 mm. Style color: White, RHS N155D. Ovary diameter: About 1 mm. Ovary color: White, RHS N155D.

Seed: None observed.

Fruit: None observed.

Disease/pest resistance: Resistance to pathogens and pests common to *Asters* has not been observed on plants grown under commercial greenhouse conditions.

Disease/pest susceptibility: Resistance to pathogens and pests common to *Asters* has not been observed on plant grown under commercial green house conditions, except mildew after flowers wilt.

High temperature tolerance: Not specifically tested, but if enough water is available, tolerant up to 35° C.

Low temperature tolerance: Not specifically tested, but if enough water is available, tolerant to −15° C.

I claim:

1. A new and distinct cultivar of *Aster* plant named 'DASDEBI', as illustrated and described herein.

* * * * *